United States Patent [19]

Cole

[11] 4,160,083

[45] Jul. 3, 1979

[54] PROCESS FOR THE SEPARATION OF ANTIBIOTIC MACROLIDES

[75] Inventor: Lucille J. Cole, Roselle Park, N.J.

[73] Assignee: Merck & Co., Inc., Rahway, N.J.

[21] Appl. No.: 838,710

[22] Filed: Oct. 3, 1977

[51] Int. Cl.$^2$ ............................................. C07H 17/08
[52] U.S. Cl. .................................. 536/17 A; 435/119; 424/181
[58] Field of Search ...................... 536/17; 260/343.41

[56] References Cited

U.S. PATENT DOCUMENTS 3,950,360  4/1976  Aoki ................................. 260/343.41

OTHER PUBLICATIONS

Mishima et al. Tetrahedron Letters 10 p. 711–714, 1975.

Journal of Antibiotics 29(6) Jun. 1976, pp. 76–36 to 76–42 and 76–14 to 76–16.

Primary Examiner—Natalie Trousof
Assistant Examiner—Jane T. Fan
Attorney, Agent, or Firm—Richard A. Thompson; David L. Rose; Harry E. Westlake, Jr.

[57] ABSTRACT

This case relates to a novel process which aids in the isolation and purification of novel compounds which are produced by the microorganism, *Streptomyces avermitilis*. The process described herein utilizes a hydroxypropyl Sephadex column chromatographic step in the isolation of the compounds from broth. The compounds which are isolated and purified are described generically s C-076 and have significant parasiticidal activity.

2 Claims, No Drawings

PROCESS FOR THE SEPARATION OF ANTIBIOTIC MACROLIDES

SUMMARY OF THE INVENTION

This invention is directed to a process for isolating the novel chemical compounds C-076 which are produced by the fermentation of a nutrient medium with a strain of the microorganism, *Streptomyces avermitilis*.

The compounds, to which the novel techniques of isolation and purification of this invention are directed, are described in co-pending U.S. application Ser. No. 772,601 of G. Albers-Schonberg, R. Burg, T. Miller, R. Ormond and H. Wallich. Said application teaches the use and characterization of the C-076 compounds as well as the utilization and characterization of the microorganism, *Streptomyces avermitilis*. Said application is hereby incorporated by reference in this application.

More particularly, this invention is comprised of a novel technique wherein it is an object of this process to aid in the isolation of the parasiticidal active compound in a substantially purified form. Further objects of this invention will become apparent from the following description.

DESCRIPTION OF THE INVENTION

In accordance with this invention, techniques of extraction and fractionation are utilized to isolate and purify substances generically described herein as C-076. These substances are prepared by growing under controlled conditions strains of microorganisms of *Streptomyces avermitilis*. These substances are described as C-076 A1a, A1b, A2a, A2b, B1a, B1b, B2a, and B2b.

Based on taxonomic studies, the microorganisms capable of producing these C-076 compounds are of a new species of the genus Streptomyces, which has been named *Streptomyces avermitilis*. One such culture, isolated from soil is designated MA-4680 in the culture collection of MERCK & CO., Inc., Rahway, N.J. A C-076 producing sample of this culture has been deposited in the permanent culture collection of the Fermentation Section of the Northern Utilization Research Branch, U.S. Department of Agriculture at Peoria, Ill., and has been assigned the accession number NRRL 8165. A sample of NRRL 8165 has also been deposited, without restriction as to availability, in the permanent culture collection of the American Type Culture Collection at 12301 Parklawn Drive, Rockville, Md. 20852, and has been assigned the accession number ATCC 31,267.

However, the present invention also embraces mutants of the above described microorganism. For example, those C-076 producing mutants which are obtained by natural selection or those produed by mutating agents including X-ray irradiation, ultraviolet irradiation, nitrogen mustard or like treatments are also included within the ambit of this invention.

One example of such an organism is a strain of *Streptomyces avermitilis* MA 4848 which was isolated after irradiation with ultraviolet light of *Streptomyces avermitilis* MA 4680. A lyophilized tube and a frozen vial of this culture has been deposited in the permanent culture collection of the American Type Culture Collection, and they have been assigned the accession numbers 31272 and 31271 respectively. Slightly higher fermentation yields of C-076 have been obtained using this frozen stock as inoculum.

In particular, this invention is directed to a process for the separation of C-076 into components A and B wherein a solution containing C-076 components is applied to a column of Sephadex LH-20 and eluted with a solvent to the said A and B components.

The elution solvent that can be utilized in the instant invention is comprised of a three-part system. One part of the system may be methylene chloride or chloroform; the second part may be hexane or heptane; and the third part may be methanol or ethanol. The ratio of the three parts may range from 8-10:8-10:0.5-2, respectively.

The column packing Sephadex LH-20 is a hydroxy propylated Sephadex. Sephadex is a dextran crosslinked with epichlorohydrin, wherein dextran is a glucose polymer.

It is often desirable to separate a small quantity of the desired compound from the fermentation broth materials as well as other compounds that may have been produced during the microorganism's elaboration period.

It is of particular interest in many cases to separate as many components from a fermentation broth as possible with as few adsorption steps as possible. This is particularly true where small quantities of the desired product are produced and recoveries may be lessened by many adsorptions and dilutions.

Sephadex LH-20 is utilized as the adsorbant in the process of this invention. This adsorbant is particularly suitable because of its partition chromatographic abilities and because small amounts of the antibiotic material are effectively separated from a large amount of impurities as well as separated into the components comprising the C-076 compounds.

The C-076 compounds are produced during the aerobic fermentation of suitable aqueous nutrient media under conditions described hereinafter, with a producing strain of *Streptomyces avermitilis*. Aqueous media such as those used for the production of many antibiotic substances are suitable for use in this process for the preparation of C-076.

Such nutrient media contain sources of carbon and nitrogen assimilable by the microorganism and generally low levels of inorganic salts. In addition, the fermentation media may contain traces of metals necessary for the growth of the microorganisms. These are usually present in sufficient concentration in the complex sources of carbon and nitrogen which may be used as nutrient sources, but can, of course, be added separately to the medium if desired.

In general, carbohydrates such as sugars, for example dextrose, sucrose, maltose, lactose, dextran, cerelose and the like, and starches are suitable sources of assimilable carbon in the nutrient media. The exact quantity of the carbon source which is utilized in the medium will depend, in part, upon the other ingredients in the medium but it is usually found that an amount of carbohydrate between about 0.5 and 5% by weight of the medium is satisfactory. These carbon sources can be used individually or several such carbon sources may be combined in the same medium.

Various nitrogen sources such as yeast hydrolysates, yeast autolysate, soybean meal, casein hydrolysates, yeast extracts, corn steep liquors, distillers solubles, cottonseed meal, meat extract and the like, are readily assimilable by *Streptomyces avermitilis* in the production of the C-076 compounds. The various sources of nitrogen can be used alone or in combination in amounts ranging from about 0.2 to 6% by weight of the medium.

Among the nutrient inorganic salts which can be incorporated in the culture media are the customary salts capable of yielding sodium, potassium, magnesium, ammonium, calcium, phosphate, sulfate, chloride, carbonate and like ions. Also included are trace metals such as cobalt, manganese, iron and the like.

The fermentation employing the C-076-producing microorganisms can be conducted at temperatures ranging from about 20° C. to about 40° C. For optimum results, it is most convenient to conduct these fermentations at a temperature in the range of from about 24° C. to about 30° C. Temperatures of about 27° C.–28° C. are most preferred. The pH of the nutrient medium suitable for producing the C-076 compounds can vary from about 5.0 to 9.0 with a preferred range of from about 6.0 to 7.5.

Small scale fermentations are conveniently carried out by placing suitable quantities of nutrient medium in a flask employing known sterile techniques, inoculating the flask with either spores or vegetative cellular growth of a C-076-producing strain of *Streptomyces avermitilis*, loosely stoppering the necks of the flask with cotton, and permitting the fermentation to proceed in a constant room temperature of about 28° C. on a rotary shaker for about 3 to 10 days. For larger scale work, it is preferable to conduct the fermentation in suitable tanks provided with an agitator and a means of aerating the fermentation medium. The nutrient medium is made up in the tank and after sterilization is inoculated with a suitable source of vegetative cellular growth of a C-076 producing strain of *Streptomyces avermitilis*. The fermentation is allowed to continue for from 1 to 8 days while agitating and/or aerating the nutrient medium at a temperature in the range of from about 24° C. to 37° C. The degree of aeration is dependent upon several factors such as the size of the fermentor, agitation speed and the like. Generally, the larger scale fermentations are agitated at about 95 to 150 rpm and about 2 to 20 cubic feet per minute of air.

The substances of this invention, which are generically referred to herein as C-076, are found primarily in the mycelium on termination of the *Streptomyces avermitilis* fermentation, and may be recovered and separated from one another as described below. Four major and four minor components of the C-076 as elaborated by *Streptomyces avermitilis* have been isolated. The eight different compounds are identified herein as C-076 A1a, A1b, A2a, A2b, B1a, B1b, B2a and B2b.

Based on experimental data, the C-076 compounds are believed to have the following planar structural formula:

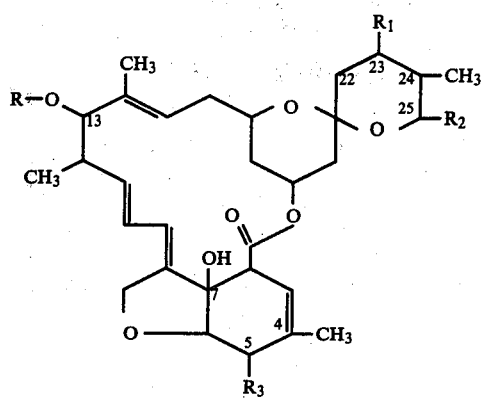

wherein R is the α-L-oleandrosyl-α-L-oleandroside of the structure:

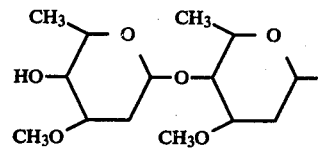

and wherein the broken line indicates a single or a double bond; $R_1$ is hydroxy and is present only when said broken line indicates a single bond.

$R_2$ is propyl or butyl; and $R_3$ is methoxy or hydroxy.

In the foregoing structural formula, the individual compounds are as set forth in Table IV.

TABLE IV

|  | $R_1$ | $R_2$ | $R_3$ |
|---|---|---|---|
| A1a | Double bond | butyl | —OCH$_3$ |
| A1b | Double bond | propyl | —OCH$_3$ |
| A2A | —OH | butyl | —OCH$_3$ |
| A2b | —OH | propyl | —OCH$_3$ |
| B1a | Double bond | butyl | —OH |
| B1b | Double bond | propyl | —OH |
| B2a | —OH | butyl | —OH |
| B2b | —OH | propyl | —OH |

The major C-076 compounds are not produced in equal amounts by the fermentations described herein. in general, it has been found that the A1 compounds comprise about 20 to 30% by weight of the total C-076 complex produced, the A2 compounds about 1 to 20% and the B1 and B2 compounds each about 25 to 35%.

The separation of the C-076 series of compounds from the whole fermentation broth and the recovery of the individual components is carried out by solvent extraction and application of chromatographic fractionations with various chromatographic techniques and solvent systems.

The C-076 compounds have slight solubility in water, but are soluble in organic solvents. This property may be conviently employed to recover them from the fermentation broth. Thus in one recovery method, the whole fermentation broth is filtered and the aqueous filtrate discarded. The wet mycelial cake is then extracted with an appropriate organic solvent. While any organic solvent may be employed, it is preferable to use a water miscible solvent such as acetone, methanol, ethanol and the like. Generally, several extractions are desirable to achieve maximum recovery. The solvent removes the C-076 active components as well as other substances lacking the antiparasitic activity of C-076. If the solvent is a water miscible one, the water is also removed from the wet mycelia. The extracted mycelia may be discarded. The solvent extracts are evaporated to remove the organic solvent and extracted several times with a second solvent. When the first extraction employs a water miscible solvent, the second extraction preferably employs a water immiscible solvent such as chloroform, methylene chloride, carbon tetrachloride, ethylacetate, methylethyl ketone, methylisobutyl ketone and the like. These latter extracts are dried and concentrated using known techniques to afford a residue comprising C-076 admixed with other materials. This fraction is then conveniently chromatographed in order to separate the active C-076 compounds from other material and also to separate and isolate the individual C-076 compounds.

Examples of such techniques are column chromatography, using such media as silica gel, aluminum oxide, dextran gels and the like, and elution of such columns with various solvents, and/or a combination of two or more solvents, in varying ratios. Liquid chromatography is employed for the detection of the C-076 compounds, and high pressure liquid chromatography may be employed to isolate purified fractions containing one or more of such compounds. Likewise, thin layer chromatography may be employed to detect the presence of, and to isolate the individual C-076 compounds. The use of the foregoing techniques as well as others known to those skilled in this art, will afford purified compositions comprising the C-076 compounds as well as the individual C-076 compounds themselves. The presence of the active C-076 compounds is determined by analyzing the various chromatographic fractions for antiparasitic activity and also by the spectral characteristics (such as ultraviolet and infrared) of said compounds as described below.

The following examples are capable of wide variation and modification, and any minor departure or extension is considered as being within the skill of the artisan and as falling within the scope of this invention.

EXAMPLE 1

A 250-ml. baffled Erlenmeyer flask containing 50 ml. of the following medium:

| | |
|---|---|
| Lactose | 2.0% |
| Distiller's Solubles | 1.5% |
| Autolyzed yeast, Ardamine pH | 0.5% |
| pH - before sterilization | 7.0 | is inoculated with the contents of one frozen vial of *Streptomyces avermitilis* MA-4848 and incubated on a rotary shaker at 28° C. for 24 hours at 150 rpm.

Ten ml. of the above fermentation media is employed to inoculate 500 ml. of the same medium as above in a 2-liter baffled Erlenmeyer flask. The fermentation media is incubated at 150 rpm on a rotary shaker at 28° C. for 24 hours.

All of the foregoing media is employed to inoculate 467 liters of the following media in a 756-liter stainless steel fermentor:

| | |
|---|---|
| Lactose | 2.0% |
| Distiller's Solubles | 1.5% |

-continued

| | |
|---|---|
| Autolyzed yeast, Ardamine pH | 0.5% |
| Polyglycol 2000 | 0.32 ml./liter |
| pH - before sterilization | 7.0 |

The fermentation media is incubated at 28° C. for 40 hours with an air flow 10 cubic feet per minute and an agitation rate of 130 rpm.

230 Liters of the above media is employed to inoculate 4,310 liters of the following medium in a 5,670-liter stainless steel fermentor:

| | |
|---|---|
| Dextrose | 4.5% |
| Peptonized Milk | 2.4% |
| Autolyzed yeast, Ardamine pH | 0.25% |
| Polyglycol 2000 | 2.5 ml./liter |
| pH - before sterilization | 7.0 |

The fermentation continues for 144 hours at 26° C. with an air flow rate of 54.3 cubic feet per minute and agitation rate of 120 rpm.

The fermentation broth is filtered and the mycelial filter cake washed with about 550 liters of water, the filtrate and washings are discarded. The filter cake is agitated with about 1500 liters of acetone for about one hour and filtered. The filter cake is washed with a mixture of about 150 liters of acetone and 40 liters of deionized water affording about 2000 liters of extract.

The foregoing fermentation and extraction is repeated on the same scale affording a further 200 liters of acetone extract which is combined with the first extract and evaporated to a volume of about 800 liters. The pH of the concentrate is adjusted to about 4.7 with concentrated hydrochloric acid and combined with about 800 liters of methylene chloride. The combined solvents are agitated for about 4 hours and separated. The aqueous layer is combined with an additional 800 liters of methylene chloride and agitated for about 4 hours. The layers are separated and each methylene chloride extract separately treated with about 10 kilograms of Super-Cel and filtered. Both extracts are evaporated to a combined volume of about 60 liters.

EXAMPLE 2

A 30-centimeter diameter column is prepared in methanol with 36 kilograms of Sephadex LH-20 (available from Pharmacia Fine Chemicals, 800 Centennial Avenue, Piscataway, New Jersey 08854) and washed with a solvent consisting of 10 parts methylene chloride, 10 parts hexane and one part methanol. One-fourth of a C-076 solution from Example 1 that has been passed through an activated alumina and an activated carbon column, concentrated in vacuo then dissolved in 10 parts methylene chloride, 10 parts hexane and one part methanol is applied to the column and the column eluted at a rate of 250 ml. per minute. Two 20-liter forecuts are collected and discarded followed by 20 2-liter rich cuts (identified as fractions 1–20), followed by a single 20-liter tail cut, which is discarded. Fractions 1–8 are found to contain the C-076 A compounds, and fractions 9–20 are found to contain the C-076 B compounds.

What is claimed is:

1. A method for the separation of C-076 compounds wherein said C-076 compounds have the formula:

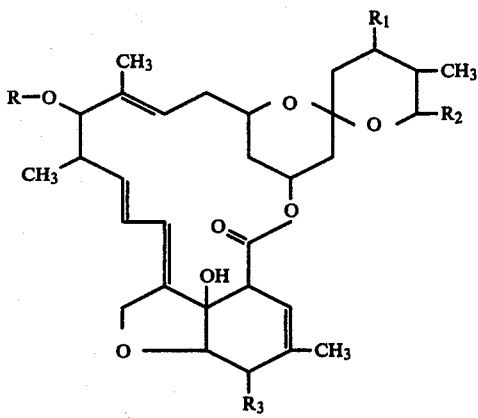

wherein R is:

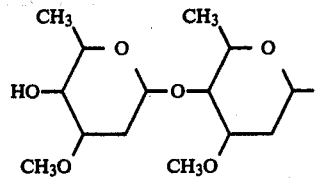

and wherein the broken line indicates a single or a double bond; $R_1$ is hydroxy an is present only when said broken line indicates a single bond.

$R_2$ is propyl or butyl; and $R_3$ is methoxy or hydroxy into components A and B from a solution containing a mixture of said components obtained from the extraction of the fermentation broth of a C-076 producing strain of *Streptomyces avermitilis* wherein said solution is applied to a column of Sephadex LH-20 and subsequently eluted with a solvent mixture of from 8 to 10 parts of methylene chloride or chloroform, from 8 to 10 parts of hexane or heptane and from 0.5 to 2 parts of methanol or ethanol.

2. The process according to claim 1 wherein the eluting solvent consists of about a 10:10:1 ratio of methylene chloride:hexanes:methanol.